(12) United States Patent
Mook et al.

(10) Patent No.: US 11,193,946 B2
(45) Date of Patent: Dec. 7, 2021

(54) BLOOD BIOMARKER FOR DISCERNING BETA AMYLOID ACCUMULATION IN BRAIN

(71) Applicant: SEOUL NATIONAL UNIVERSITY R&DB FOUNDATION, Seoul (KR)

(72) Inventors: Inhee Mook, Seoul (KR); Sun-Ho Han, Seoul (KR); Jong-Chan Park, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 218 days.

(21) Appl. No.: 16/496,547

(22) PCT Filed: Mar. 22, 2018

(86) PCT No.: PCT/KR2018/003340
§ 371 (c)(1),
(2) Date: Sep. 23, 2019

(87) PCT Pub. No.: WO2018/174585
PCT Pub. Date: Sep. 27, 2018

(65) Prior Publication Data
US 2021/0215719 A1    Jul. 15, 2021

(30) Foreign Application Priority Data
Mar. 23, 2017    (KR) .................. 10-2017-0036625

(51) Int. Cl.
*G01N 33/68*    (2006.01)
*C12Q 1/6883*    (2018.01)
*G01N 33/78*    (2006.01)
*G01N 33/84*    (2006.01)
*G01N 33/92*    (2006.01)

(52) U.S. Cl.
CPC ....... *G01N 33/6896* (2013.01); *C12Q 1/6883* (2013.01); *G01N 33/78* (2013.01); *G01N 33/84* (2013.01); *G01N 33/92* (2013.01); *C12Q 2600/118* (2013.01); *G01N 2800/2821* (2013.01); *G01N 2800/52* (2013.01)

(58) Field of Classification Search
CPC ....... G01N 33/6896; G01N 2800/2821; G01N 2800/52; G01N 33/68; G01N 2333/78; C12Q 1/6883; C12Q 2600/158; C12Y 301/01007
See application file for complete search history.

(56) References Cited

U.S. PATENT DOCUMENTS 6,136,548 A * 10/2000 Anderson .............. A61K 38/49
435/226

FOREIGN PATENT DOCUMENTS

| KR | 10-2010-0049363 A | 5/2010 |
|---|---|---|
| KR | 10-2014-0042331 A | 4/2014 |

OTHER PUBLICATIONS

Han et al. Blood acetylcholinesterase level is a potential biomarker for the early detection of cerebral amyloid deposition in cognitively normal individuals, Neurobiology of Aging, vol. 73, 2019, pp. 21-29. https://doi.org/10.1016/j.neurobiolaging.2018.09.001.*
Kang et al. PiB-PET Imaging-Based Serum Proteome Profiles Predict Mild Cognitive Impairment and Alzheimer's Disease. J Alzheimers Dis. Jul. 6, 2016;53(4):1563-76. doi: 10.3233/JAD-160025.*
Park et al. Prognostic plasma protein panel for Aβ deposition in the brain in Alzheimer's disease, Progress in Neurobiology, vol. 183, 2019, 101690. https://doi.org/10.1016/j.pneurobio.2019.101690.*
Galasko et al., "High Cerebrospinal Fluid Tau and Low Amyloid beta42 Levels in the Clinical Diagnosis of Alzheimer Disease and Relation to Apolipoprotein E Genotype", Arch Neurol., (1998), vol. 55, pp. 937-945.
Han et al., "Human Serum Transthyretin Levels Correlate Inversely with Alzheimer's Disease", Journal of Alzheimer's Disease, (2011), vol. 25, pp. 77-84.
Li et al., "Neuronal Production of Transthyretin in Human and Murine Alzheimer's Disease: Is It Protective?", The Journal of Neuroscience, (2011), vol. 31, No. 35, pp. 12483-12490.

* cited by examiner

*Primary Examiner* — Gregory S Emch
(74) *Attorney, Agent, or Firm* — Vorys, Sater, Seymour & Pease LLP; Mih Suhn Koh

(57) ABSTRACT

Provided concerns a blood biomarker for discerning the cerebral deposition of amyloid beta, which is a causative material of Alzheimer's dementia. A marker according to the subject matter can conveniently and rapidly predictive of cerebral amyloid beta accumulation by use of a blood and can be effectively used in diagnosing relevant diseases including mild cognitive impairment at a preclinical level.

4 Claims, 16 Drawing Sheets

Different composition of biomarkers for different disease models

Different composition of biomarkers for different disease models

Blood level of AchE in AchE inhibitor non-taker

BLOOD BIOMARKER FOR DISCERNING BETA AMYLOID ACCUMULATION IN BRAIN

BACKGROUND OF THE INVENTION

Field of the Invention

The present application relates to biomarkers that can be measured in blood, which can be used to measure amyloid beta accumulation in the brain. This method also can be used to aid in the detection of neurodegenerative diseases, including Alzheimer's disease and Mild Cognitive Impairment.

Description of the Related Art

BACKGROUND OF THE INVENTION

Alzheimer's disease (AD) is one of the most prevalent neurodegenerative diseases in the elderly. AD, an age-associated dementing disorder, currently affects more than 20% of population aged over 80. The number of AD patients increase rapidly along with population aging. Amyloid beta (Aβ) plaques (senile plaque) and neurofibrillary tangles (NTF) of hyper phosphorylated tau proteins are the major pathological hallmarks of AD. Aβ accumulation occurs in the early stages of AD, and play critical roles in initiating AD pathogenesis. The pathological changes in AD brain were caused by several environmental and genetic factors. Unfortunately, there is no clear way to diagnose and treat AD yet.

Currently, the most common AD diagnostic methods are brain imaging methods [MRI(Magnetic Resonance Imaging), PET (Positron Emission Tomography)] and cognitive evaluating methods such as MMSE (Mini Mental State Examination). Diagnosis through the MMSE method can have different results depending on age, education, etc. Diagnosis through MRI and/or PET is more expensive than other methods. Detection methods for both senile plaque and NTF in brain biopsies are being used. However, there is currently no clear AD diagnosis tool or detection method for AD progress.

The search for AD diagnostic biomarkers using blood, cerebrospinal fluid (CSF) and other type of body fluids etc. is an important research field. CSF, as it is in direct contact with brain cells, can reflect change of brain protein level. In the CSF of AD patients, Aβ42 concentration was reduced compared to the normal elderly. In addition, an increase in total tau protein and phosphorylated tau protein has been reported. However, as most AD patients are over 65 years old, the lumbar puncture to obtain CSF from AD patients is very dangerous.

Pittsburgh compound B (PIB), a newly developed compound can specifically bind to amyloid beta, which accumulates in the brain as AD pathology progresses. PIB is a useful substance for AD diagnosis. Analysis of brain PET image obtained after administration of radio-labeled PIB through the vein of AD patients tells us how much amyloid beta has accumulated in the subject brain. Thus, PIB-PET can be used as an effective AD diagnostic tool. However, this diagnostic method is very expensive, and needs high quality equipment. This diagnostic tool cannot be a widespread AD diagnostic method.

Compared to brain imaging technology, diagnostics using blood biomarkers have many advantages: relatively easy sample collection, cost effective test, time-saving etc. Blood diagnostic markers should reflect brain functional pathological change according to AD progression. However, it is difficult to get appropriate blood biomarkers for AD because they do not always show the correlation between pathological change of brain function and AD progression. Generally, when brain proteins that reflect AD progression increase or decrease in the brain, it respectively decreases or increases in CSF and blood. For example, as AD progresses, the levels of A1342 in the brain increase while the it is reduced in CSF; Transthyretin increases in the brain, while it decreases in the blood [Scheuner et al., Nature Medicine 2, 864-870 (1996); Galasko et al., Arch Neurol 55 (7): 937-45 (1998); Li et al., Journal of Neuroscience 31 (35): 12483-12490 (2011); and Han et al., Journal of Alzheimer disease 25 (1) 77-84 (2011)].

Republic of Korea Patent Publication No. 2012-0041823 discloses protein biomarkers for early diagnosis of AD such as ATP synthase subunit beta, adenosine kinase (Long Isoform), and regucalcin.

Republic of Korea Patent Publication No. 2010-0049363 discloses AD diagnostic kit and apparatus using vitamin D binding protein and its binding antibody. Republic of Korea Patent Publication No. 2014-0042331 discloses multiple biomarkers for cognitive disorder. It discloses useful biomarkers and the usage of biomarkers for cognitive disorders: Transthyretin, ApoE, α-synuclein, vitamin D binding protein, neurogranin, vimentin, stathmin, contactin, and HDL-cholesterol.

It is very difficult to diagnose of AD early. After AD progresses, the social cost will be very high. Normal life cannot be carried out with severe case of AD. Therefore, easy-to-use methods such as blood tests must be developed to diagnose AD early, test for severity and even diagnose before symptoms appear (preclinical).

Recently, active research has identified various AD diagnostic blood biomarker candidates, but each did not meet required standards in sensitivity and accuracy of diagnostic power.

SUMMARY OF THE INVENTION

Technical Problem

The present application provides methods for prediction of brain amyloid beta plaque accumulation and/or diagnosing amyloid beta related disease using blood biomarkers.

Technical Solution

One in the embodiment herein, from the group of markers that consists of Periostin, VE-cadherin, Acetylcholinesterase (ACHE), Thrombospondin-1 (TSP-1), serum amyloid beta, LGALS3BP (Lectin, galactoside-binding, soluble3 binding protein) and Angiotensin I converting enzyme (ACE), one or more of the markers in the blood has a purpose to detect: among the above markers, plasma amyloid beta, LGALS3BP, ACE and ACHE are selected for prediction of brain amyloid beta accumulation and detection of the normal cognitive function group; among the above markers, plasma amyloid beta, LGALS3BP, ACE, Periostin and VE-cadherin are selected for prediction of brain amyloid beta accumulation and detection of the mild cognitive impairment patients group; among the above markers, plasma amyloid beta, LGALS3BP and ACE are selected for prediction of brain amyloid beta accumulation and detection of non-demented group including cognitive normal group and mild cognitive impairment patients group; among the above markers, plasma amyloid beta, LGALS3BP, ACE and TSP-1 are selected for prediction of brain amyloid beta accumulation and detection of all group including non-demented group and AD group.

In other embodiment herein, this invention provides composition of materials to detect amyloid beta accumulation, kit or methods that include all materials to detect the above biomarkers, In one embodiment, the plasma amyloid beta in the marker according to the invention is treated with MPP (Protease inhibitor and phosphatase inhibitor cocktail, see Example 1-4).

In one embodiment, the markers according to the present application can be detected in the blood, particularly in plasma.

In one embodiment, the markers according to the present application may further comprise ApoE in addition to above markers.

In one embodiment, the cognitive normal group in which the marker is used in the method according to the invention is in particular an Acetylcholinesterase Inhibitor (AchEI) untreated group.

In one embodiment, the marker according to the present application may further include free triiodothyronine (T3) and/or High Density Lipoprotein (HDL) cholesterol, which are common test item of blood tests, in addition to above markers.

In another embodiment, the markers according to the present application are used for the diagnosis of a disease related to brain amyloid beta accumulation or to determine whether PIB-PET test is necessary, wherein the brain amyloid beta accumulation disease is an amyloid diseases caused by amyloid beta accumulation include, but are not limited to, AD, Parkinson's dementia, Lewy body dementia, Huntington's dementia, or preclinical AD, down syndrome, or cognitive impairment.

In one embodiment, the markers according to the invention can also be used to determine the severity of cognitive impairment in diagnosing brain amyloid beta accumulation disease.

In another embodiment herein, the present invention also provides a method of providing a blood sample from a test subject in need of detection of accumulation of brain amyloid beta. In the step of quantifying, one or more markers are selected from the group that consists of Periostin, VE-cadherin, ACHE, TSP-1, plasma amyloid beta, LGALS3BP and ACE: wherein the plasma amyloid beta, LGALS3BP, ACE and ACHE are quantified from blood samples of the cognitive function group; wherein LGALS3BP, ACE, Periostin and VE-cadherin are quantified from blood samples of the mild cognitive impairment patient group; wherein plasma amyloid beta, LGALS3BP and ACE are quantified from blood samples of the normal and mild cognitive impairment group, and wherein plasma amyloid beta, LGALS3BP, ACE and TSP-1 are quantified from blood samples of all groups. The quantity of each biomarker reflects brain amyloid beta accumulation. This invention provides a method for detecting brain amyloid beta accumulation using blood biomarkers. The method includes the step to associate the amount of each biomarker with whether brain amyloid beta has accumulated in the brain.

The step of associating in the method according to the present invention is determined by the amount of each marker of test subjects compared with the quantitative results in the control group: when the Periostin is increased while LGAL, ACE, AChE, TSP1, and VE-cadherin are all reduced, the test subject is thought to have amyloid beta accumulation in brain. This is the additional determining step.

The method according to the invention can also be used for the diagnosis of diseases associated with brain amyloid beta accumulation, for deciding whether PIB-PET testing is required, or for determining the severity of cognitive impairment.

In one embodiment, the markers in the method according to the invention can also be used to diagnose diseases associated with brain amyloid beta accumulation and to determine cognitive impairment severity.

In one embodiment, the markers according to the present application can be detected in the blood, particularly in plasma.

In one embodiment, the markers according to the present application may further comprise ApoE in addition to above biomarkers.

In one embodiment, the cognitive normal group in which the marker is used in the method according to the invention is in particular an AchEI (inhibitor) untreated group.

In another embodiment, the present invention provides Periostin, VE-cadherin, Acetylcholinesterase (ACHE), Thrombospondin-1 (TSP-1), Plasma amyloid beta, LGALS3BP (Lectin, galactoside-binding, soluble3 binding protein) for detecting brain amyloid beta accumulation as blood biomarkers. The markers of the plasma amyloid beta, LGALS3BP, ACE and ACHE are selected for prediction of brain amyloid beta accumulation and detection of the normal cognitive function group. The markers of the plasma amyloid beta, LGALS3BP, ACE, Periostin and VE-cadherin are selected for prediction of brain amyloid beta accumulation and detection of the mild cognitive impairment patients group. The markers of plasma amyloid beta, LGALS3BP and ACE are selected for prediction of brain amyloid beta accumulation and detection of non-demented group including cognitive normal group and mild cognitive impairment patients group. The markers of the plasma amyloid beta, LGALS3BP, ACE and TSP-1 are selected for prediction of brain amyloid beta accumulation and detection of all groups including non-demented group and Alzheimer's disease group.

In one embodiment, this invention provides the MPP treated plasma amyloid beta as a biomarker for brain amyloid beta accumulation.

In one embodiment, AchE inhibitor untreated normal cognitive function group provides the biomarkers for detecting brain amyloid beta accumulation.

In one embodiment, this invention provides the markers for detecting brain amyloid beta accumulation of normal cognitive function group, mild cognitive impairment group, non-dementia group and dementia group. The markers may further comprise ApoE in addition to above biomarkers.

In one embodiment, the markers for detecting brain amyloid beta accumulation in the normal cognitive function group, mild cognitive impairment group, non-dementia group and dementia group additionally includes at least one of following biomarkers: phosphorus, HDL (High Density Lipoprotein), and free T3 (free triiodothyronine).

In one embodiment, brain amyloid beta accumulation is used to diagnose a disease associated with brain amyloid beta accumulation, or to determine whether a Pittsburgh compound B (PIB)—positron emission tomography (PET) test is required. The biomarkers provide a way of detecting brain amyloid beta accumulation in disease which includes Alzheimer's disease, Parkinson's dementia, Lewy body dementia, Huntington's disease dementia, or preclinical Alzheimer's disease, Down syndrome, or cognitive impairment.

In one embodiment, biomarkers are provided to diagnose diseases associated with brain amyloid beta accumulation, including determining the severity of cognitive impairment.

Effect of Invention

The biomarker according to the present invention can detect brain accumulation of amyloid beta, which is a cause of Alzheimer's dementia, easily and quickly in the blood at an early stage.

Accumulation of amyloid beta in the brain begins 15-20 years before clinical symptoms such as dementia and forgetfulness appear. The markers according to the present application, which can confirm the accumulation of brain amyloid beta through blood tests of patients with non clinical symptoms or mild clinical symptoms, is applicable to detect Alzheimer's disease early, as well as to offer a chance to slow or prevent its progression at early stage. Early stage diagnosis of AD can dramatically improve the quality of life of the patient.

Furthermore, the panel of markers according to this invention may be composed of more effective combinations of defined groups according to the degree of cognitive function, for example: cognitive normal group, mild cognitive impairment group, Alzheimer's dementia group, and all progress stage groups. The diagnostic power can be improved using analysis of combination group study.

In addition, the biomarker according to the present application can be effectively used to replace PIB-PET imaging or to screen for which patients need it. PIB-PET imaging is an expensive test that can be performed only in some university hospitals that can confirm the accumulation of brain amyloid beta with brain imaging. Therefore, the blood biomarkers according to the present invention, which can easily confirm accumulation of brain amyloid beta in blood, is very effective in terms of convenience and cost reduction of patients.

BRIEF DESCRIPTION OF THE DRAWINGS

FIG. 1a is a PET image of the beta amyloid accumulation by each test subject group herein. PET imaging is a standard measure method of brain beta amyloid accumulation and can be linked to blood biomarkers and amyloid beta accumulation in the brain. FIGS. 1b and 1c show markers for each model according to the segmented patient group. Periostin increases in PIB-PET positive group, and LGAL, ACE, AChE, TSP1, and VE-cadherin all decrease in PIP-PET positive group. This indicates a high correlation between the PIB-PET result and the marker according to the present application, which indicates that the marker according to the present invention can be usefully used for beta amyloid accumulation in the brain.

The quantitative value of LGALS3BP in normal cognitive function group, mild cognitive impairment group, Alzheimer's dementia group, and all stages group was significantly decrease in amyloid beta positive groups compare to in amyloid beta negative groups. Therefore, it can be used for models 1 through 4 according to the present application. These quantitative values were also used to determine specificity, sensitivity, and AUC values through the use of logistic regression equations to calculate integrated indices (see Example 2) and analyze ROC curves.

Figure 7:
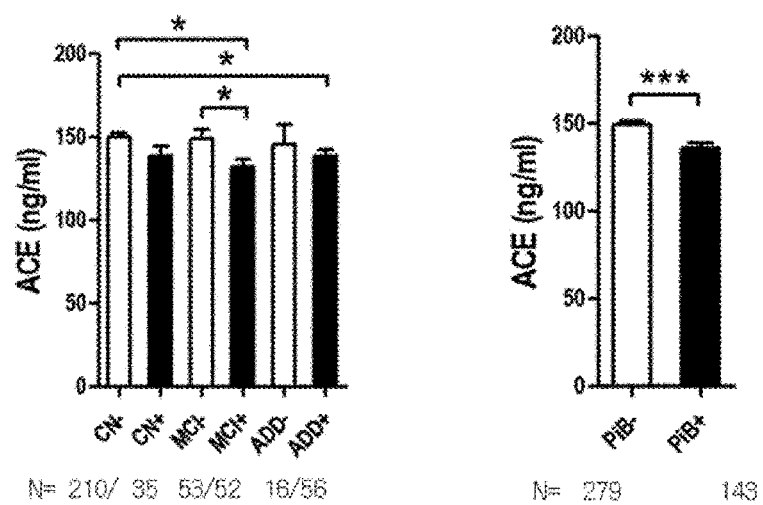

FIG. 7 shows the results of quantification of ACE by ELISA in normal cognitive function (CN), mild cognitive impairment (MCI), Alzheimer's dementia (ADD), and all stages (PIB− vs PIB+) blood.

The quantitative value of ACE was compared in the normal cognitive function group, mild cognitive impairment, Alzheimer's dementia group, and all stages group. It shows a significant change and shows a tendency to decrease in MCI and all amyloid beta positive groups. It can be used for model 1 through 4 according to the present application. These quantitative values were also used to determine specificity, sensitivity, and AUC values through the use of logistic regression equations to calculate integrated indices (see Example 2) and analyze ROC curves.

Figure 8:
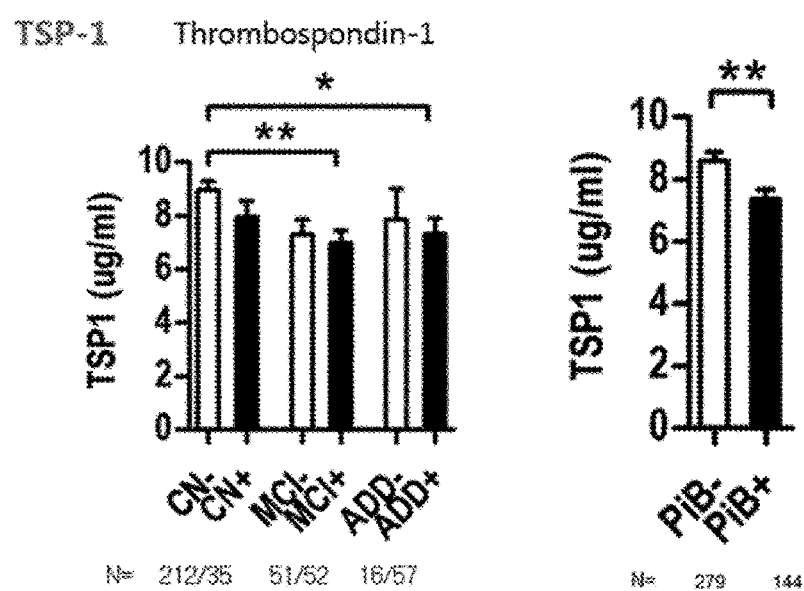

FIG. 8 shows experimental results of quantifying TSP-1 by ELISA in normal cognitive function (CN), mild cognitive impairment (MCI), Alzheimer's dementia (ADD), and all (PIB− vs PIB+) blood.

The quantitative value of TSP-1 was compared in the normal cognitive function group, mild cognitive impairment, Alzheimer's dementia group, and all group. It shows a significant change and shows a tendency to decrease in all amyloid beta positive groups. It can be used for model 4 accordingly. These quantitative values were also used to determine specificity, sensitivity, and AUC values through the use of logistic regression equations to calculate integrated indices (see Example 2) and analyze ROC curves.

Figure 9:
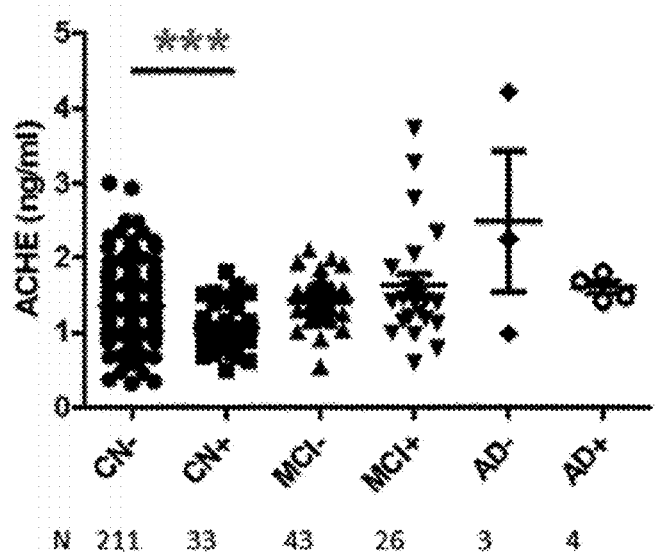

FIG. 9 is a test result of quantifying AChE by ELISA in blood of normal cognitive function group (CN), mild cognitive impairment (MCI), Alzheimer's dementia group (ADD). The quantitative value of AChE was compared in the normal cognitive function group, mild cognitive impairment, and Alzheimer's dementia group. It shows a significant change and shows a tendency to decrease only in normal cognitive function group with brain amyloid beta accumulation (Aβ+). It can be used for model 1 accordingly. These quantitative values were also used to determine specificity, sensitivity, and AUC values through the use of logistic regression equations to calculate integrated indices (see Example 2) and analyze ROC curves. Blood from AChE inhibitor (AChEI) untreated group was used in this experiment. AChE is useful marker for discriminating Aβ positive or negative in normal cognitive function group because more than half of MCI patients or almost all AD patients are taking AChE inhibitors. If test subject is taking AChE inhibitors, it is difficult to determine whether there is a change in blood AChE levels due to brain amyloid accumulation. Normal cognitive function group that does not take AChE inhibitors, the quantitative values of AChE can be used to confirm the association with brain amyloid beta accumulation.

Figure 10:
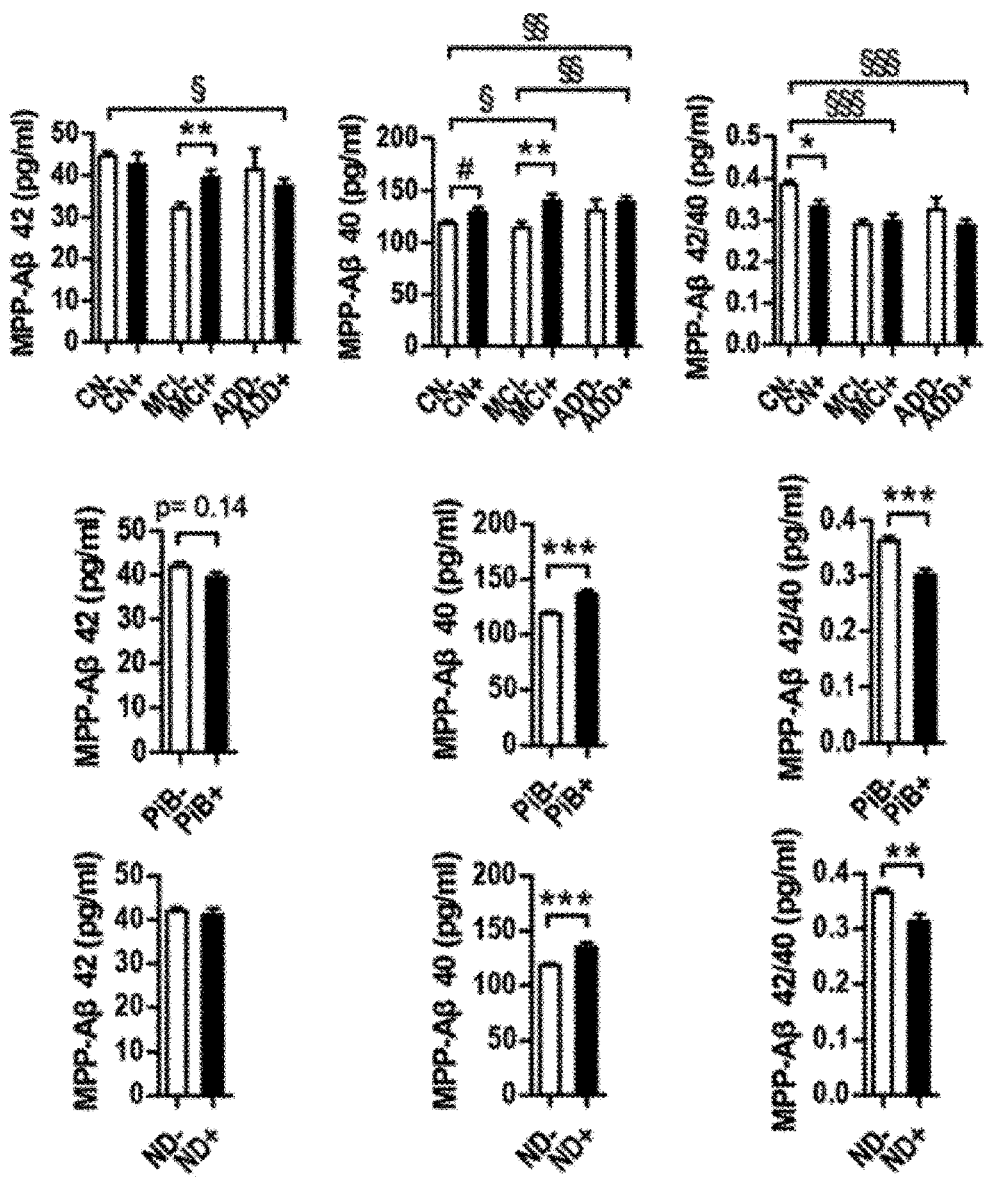

FIG. 10 shows the results of quantifying MPP-amyloid beta by ELISA in normal cognitive function (CN), mild cognitive impairment (MCI), Alzheimer's dementia (ADD), and total (PIB− vs PIB+) blood. The quantitative value of ratio of Aβ42/Aβ40 was compared in the normal cognitive function group, mild cognitive impairment, Alzheimer's dementia group, and all progress stage group. The ratio of Aβ42/Aβ40 was significant decrease in Aβ positive groups of normal cognitive function group and PIB positive group of all, indicating that it can be used in models 1 through 4 according to the present application. These quantitative values were also used to determine specificity, sensitivity, and AUC values through the use of logistic regression equations to calculate integrated indices (see Example 2) and analyze ROC curves.

DETAILED DESCRIPTION OF THE EMBODIMENTS

The present application, on the basis of cognitive function and PIB PET imaging, conducted large-scale cohort, individual verification from 6 groups of patients to discover biomarkers for periostin, VE-cadherin, ACHE (Acetylcholinesterase), TSP-1 (Thrombospondin-1), LGALS3BP (Lectin, galactoside-binding, soluble3 binding protein) and ACE (Angiotensin I converting enzyme) which have a significant correlation with the accumulation or aggregation of amyloid beta in brain. Furthermore, the above markers can be grouped into more affective combinations for each specific patient. Using this aspect, it is possible to use more accurate and effective biomarkers for each patient group, which means that it is a marker that can be used to predict whether amyloid beta is accumulated in all populations such as normal groups, mild cognitive impairment groups, and Alzheimer's disease group.

In one embodiment, this invention provides herein a group of biomarkers such as Periostin, VE-cadherin, ACHE (Acetylcholinesterase), TSP-1 (Thrombospondin-1), plasma amyloid beta, LGALS3BP (Lectin, galactoside-binding, soluble3 binding protein) and ACE (Angiotensin I converting enzyme). It relates to the use for the discrimination or determination of the accumulation of amyloid beta in brain using one or more markers selected from the above group of biomarker.

Such use is intended for use in a composition comprising a detection material capable of detecting the marker in vitro or in vivo, in the form of a kit, or in the form of a composition comprising the marker itself, or a method for detecting beta amyloid accumulation using the marker. It may be implemented in the any form.

To date, detection or prediction of amyloid beta plaque accumulation has been confirmed by detection of amyloid beta plaque accumulation by post-mortem brain biopsy of Alzheimer's dementia patients and confirmed Alzheimer's dementia. Recently, a technology such as PIB-PET has been developed that can confirm the accumulation of brain amyloid beta in brain imaging, but it is a very expensive test, using expensive equipment that can be performed only in some university hospitals, and also causes inconvenience to patients during the test. Therefore, the blood biomarker according to the present application which can confirm the accumulation of brain amyloid beta is very important.

Accumulation of brain amyloid beta begins 15-20 years before clinical symptoms such as dementia or forgetfulness. If it is possible to detect brain amyloid beta accumulation from preclinical stage Alzheimer's disease patients, doctors can diagnose Alzheimer's dementia early and slow or stop its progress at an early stage. Also, it is possible to identify patients with Alzheimer's disease that does not accumulate brain amyloid beta yet, thus the treatment strategy can be changed to more effective treatment for these patients.

In addition, detection of amyloid beta accumulation in the brain using the markers according to this invention can also be used for the diagnosis of diseases caused by the accumulation of amyloid beta.

Various diseases caused by the accumulation of amyloid beta in the brain have been known [Head, E., and Lott, I. T. (2004) Down syndrome and beta-amyloid deposition. Cur Opin Neurol 17; Primavera et al., (1999) Brain Accumulation of Amyloid-beta in Non-Alzheimer Neurodegeneration. J Alzheimers Dis; Masliah et al., (2001) beta-amyloid peptides enhance alpha-synuclein accumulation and neuronal deficits in a transgenic mouse model linking Alzheimer's disease and Parkinson's disease. Proc Natl Acad Sci], thus markers according to this invention can also be used for the diagnosis, detection, etc. of various diseases associated with brain amyloid beta accumulation.

In one embodiment, the diseases associated with such brain amyloid beta accumulation include, for example, Alzheimer's disease, Parkinson's dementia, Lewy body dementia, Huntington's disease dementia, or preclinical Alzheimer's disease, down syndrome, or cognitive impairment.

The term "cognitive impairment" herein refers to neurodegenerative diseases, for example, Alzheimer's (AD) dementia, Parkinson's dementia, Lewy body dementia, Huntington's disease dementia, Alzheimer's dementia (ADD) group; it also includes mild cognitive impairment (MCI: Mild Cognitive Impairment), which is a stage before progression to dementia, and in this sense, may include both dementia and non-dementia groups. The severity of cognitive impairment can be classified by methods such as Mini Mental State Examination (MMSE) score [Benson et al., (2006) Journal of clinical Psychiatry, Bryant et al., (2008) Arch Neurol].

Herein "Dementia" includes Alzheimer's disease, Parkinson's disease dementia, Lewy body dementia, or Huntington's disease dementia.

"Non-dementia" as used herein includes the normal cognitive function group and the mild cognitive impairment group.

In the present application, "normal cognitive function group" refers to a group in which cognitive function is determined to be normal through a test such as MMSE, regardless of whether beta amyloid accumulates. This definition includes normal individuals without brain cognitive decline with or without brain amyloid beta accumulation. Since amyloid beta accumulates in the brain of normal cognitive function group, it can progress to dementia through mild cognitive impairment. Therefore, it is very important to detect amyloid beta accumulation in the normal cognitive function group for demanding early detection of dementia.

The term "mild cognitive impairment group" in the present application includes both a preliminary stage of dementia with cognitive impairment but with no brain amyloid beta accumulation and a pre-dementia with cognitive impairment with brain amyloid beta accumulation who can manage normal life.

In this regard, the degree of cognitive decline is enhanced in this order of dementia groups: normal cognitive functional groups, mild cognitive impairment groups and Alzheimer's dementia (ADD) groups.

Herein this invention "the dementia patient group" includes individuals with cognitive impairment that show signs of Alzheimer's dementia (ADD) and has been diagnosed with dementia, with or without brain amyloid beta accumulation.

In the present application, the "all progress stage groups" includes all patient groups that lead up to being diagnosed with dementia, and includes a normal cognitive function group, a mild cognitive impairment group, and a dementia patient group. It also includes both PIB-PET positive and negative patients.

In one embodiment according to the invention in particular, the dementia is Alzheimer's dementia.

In the present application, Alzheimer's dementia or Alzheimer's disease is a neurodegenerative brain disease with a progressive decline of cognitive function including memory, also called AD or ADD (Alzheimer's dementia). This may include preclinical Alzheimer's disease before the onset of clinical symptoms, as well as mild cognitive impairment, which is a stage prior to dementia. The pathological hallmarks of Alzheimer's disease are senile plaques and neurofibrillary tangle, which are characterized by the deposition of amyloid beta protein and the hyperphosphorylation and inflammation of tau protein, respectively. It is also known to be due to oxidation reaction and oxidative damage. The preclinical Alzheimer's disease refers to a stage in which amyloid plaque deposition in the brain appears, although there is no clinical symptom.

In this invention, the "amyloid beta plaque" or "beta amyloid plaque" means an insoluble fibrous protein aggregate comprising amyloid beta, also referred to herein as AO, the main component being A040 or A042. In one embodiment, the amyloid plaques may be present in cells, on the cell surface, and/or in spaces between cells. In particular, it exists in the spaces between cells of neural tissues, and it is used as a marker for diagnosing Alzheimer's dementia. The diagnosis of dementia according to the degree of amyloid plaque accumulation can be referred to the disclosure [Mawuenyega et al., (2010) Science; Querfurth and LaFerla, (2010) The New England journal of medicine]. Amyloid beta plaques according to the context may be referred to as amyloid beta, which will be readily appreciated by those skilled in the art.

As used herein, the term "diagnosis" refers to determining the susceptibility of a subject, or subject, to a particular disease or disorder, to determine whether a subject currently has a particular disease or disorder, or to a particular disease or disorder. Also, refers to determining the prognosis of one object at hand or therametrics (eg, monitoring the condition of the object to provide information about treatment efficacy).

"Early diagnosis" herein includes diagnosing at the preclinical stage, at mild cognitive impairment stage, or before clinical symptoms appear.

As used herein, the term "diagnosis marker or diagnostic marker" refers to a substance that can be diagnosed by distinguishing Alzheimer's disease from normal, and includes a protein showing an increase and/or decrease in blood of a subject with a disease as compared to an appropriate control group. Among biomarkers according to the present invention, Periostin concentration in blood increases with accumulation of amyloid beta plaque, and LGALS3BP, ACE, AChE, TSP1, and VE-cadherin concentration in blood decreases with accumulation of amyloid beta plaque (see FIGS. 6 to 10). The markers used further in addition to the markers herein, are phosphorus, free T3, and HDL cholesterol. Compared with the results of normal control or PIB-PET negative subjects, blood phosphorus, free T3 concentration is lowered while HDL cholesterol concentration is significantly higher in subject who with brain amyloid beta accumulation.

The amino acid sequences of protein and nucleic acid sequences, intracellular processing, modification, etc. of markers Periostin, VE-cadherin, ACHE, TSP-1, LGALS3BP and ACE according to the present invention are as shown below in Table 1, Those skilled in the art will be able to readily select the sequences and detection methods necessary for detecting the markers.

TABLE 1

| Biomarker according to the present invention | Uniprot ID https://www.uniprot.org/uniprot/Q15063 |
| --- | --- |
| Periostin | Q15063 |
| VE-cadherin | P33151 |
| ACHE | P22303 |
| TSP-1 | P07996 |
| LGALS3BP | Q08380 |
| ACE | P12821 |

Plasma amyloid beta in the markers according to the present invention is a plasma pretreatment composition (MPP) treated with a mixture of protease inhibitors and phosphatase inhibitors. For this, reference may be made to what is disclosed in detail in Korean Patent Application Publication No. 2016-0129444 filed by the original inventor.

Markers according to the invention are especially detected in blood samples. A blood sample can be obtained very easily compared to collection of CSF used for the diagnosis of dementia. Diagnosis of dementia using blood samples greatly reduced in cost and increases convenience. Samples in which the markers according to the invention are used include, but are not limited to, whole blood, platelets, and plasma or serum samples. In one embodiment, plasma is used. As used herein, for comparative analysis, specimens from test subjects in need of diagnosis or detection, as well as samples from a normal control group or a control group having a specific disease, can also be used.

In particular, the markers of the present application are combined with markers according to the patients classified according to the degree of cognitive decline, that is, the normal cognitive function group, the mild cognitive impairment group, or the all progress stage group, and thus it is possible to discriminate amyloid beta positive or negative in each subject group with improved accuracy and effectiveness.

In one embodiment, the amyloid beta, LGALS3BP, ACE and ACHE of the markers according to the present application are used to detect brain amyloid beta accumulation in the normal cognitive function group. In one embodiment, in particular, the ACHE marker is used in patients not taking an ACHE inhibitor.

In another embodiment, amyloid beta, LGALS3BP, ACE, Periostin and VE-cadherin of the markers according to the present invention is used for the detection of brain amyloid beta accumulation in the mild cognitive impaired patient group.

In another embodiment, the plasma amyloid beta, LGALS3BP, and ACE in the markers according to this invention are used for detecting whether brain amyloid beta accumulates in the non-dementia group including the cognitive normal group and the mild cognitive impairment group.

In another embodiment, plasma amyloid beta, LGALS3BP, ACE and TSP-1 of the marker according to the present invention is used for the detection of the accumulation of brain amyloid beta in the all progress stage groups including the non-dementia group and dementia group.

In another embodiment, plasma amyloid beta, LGALS3BP, ACE and TSP-1 are used to detect brain amyloid beta accumulation throughout the all progress stage group, including non-dementia and dementia groups.

In another embodiment, the marker according to the present application may further include ApoE genotyping, which will be described later, in the detection markers of the respective groups.

In another embodiment, the marker according to this invention may include, as additional markers, the detection markers of the respective groups, phosphorus, free T3 and/or HDL cholesterol, which are items measured in a conventional blood test described below. Such markers can be used in the presence or absence of ApoE genotyping.

In addition, the marker of the present application may be an indicator for the onset and progression of the cognitive impairment, and may be used for the onset, the progression of the disease, the diagnosis or prognosis of the disease.

Thus, in another aspect, the present application can be used to determine whether a marker or combination of markers as described above is necessary for the prediction of amyloid beta plaque accumulation, early diagnosis, or PIB-PET imaging testing. For example, in the blood test using the marker according to the present application, it is not necessary to test the PIB-PET image when it is determined that amyloid beta is not accumulated in the brain. If it is determined that amyloid beta has accumulated in brain, PIB-PET imaging can be done to confirm the diagnosis.

Figure 1A:
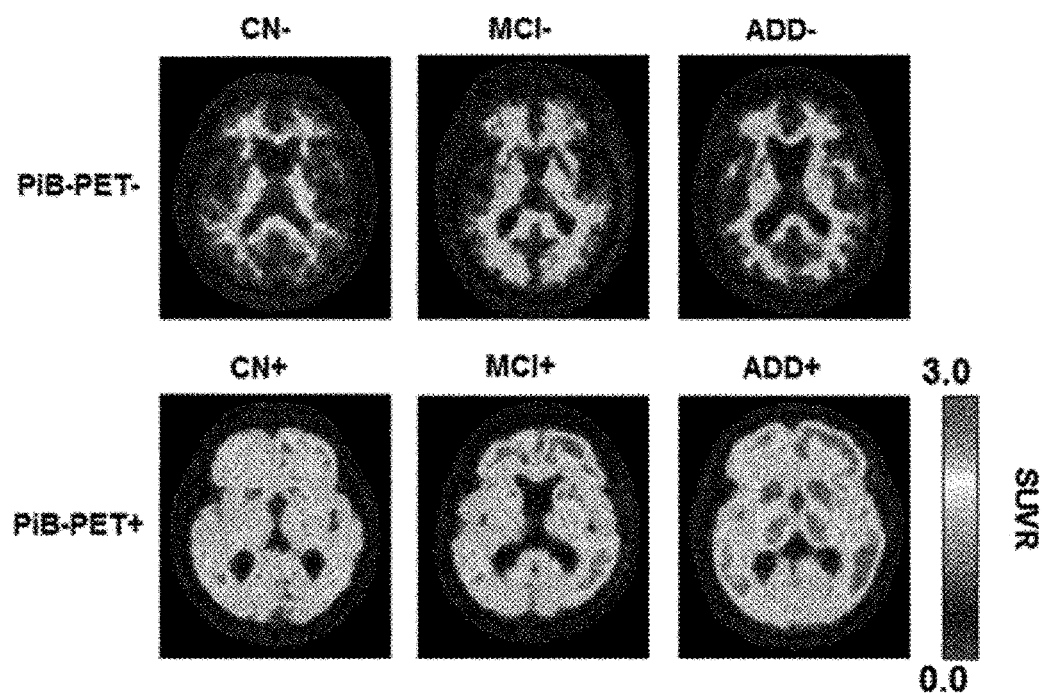
FIGS. 1a, 1b and 1c schematically show a model established for differentiating brain beta amyloid accumulation through the biomarker detection in the blood.
Figure 1B:
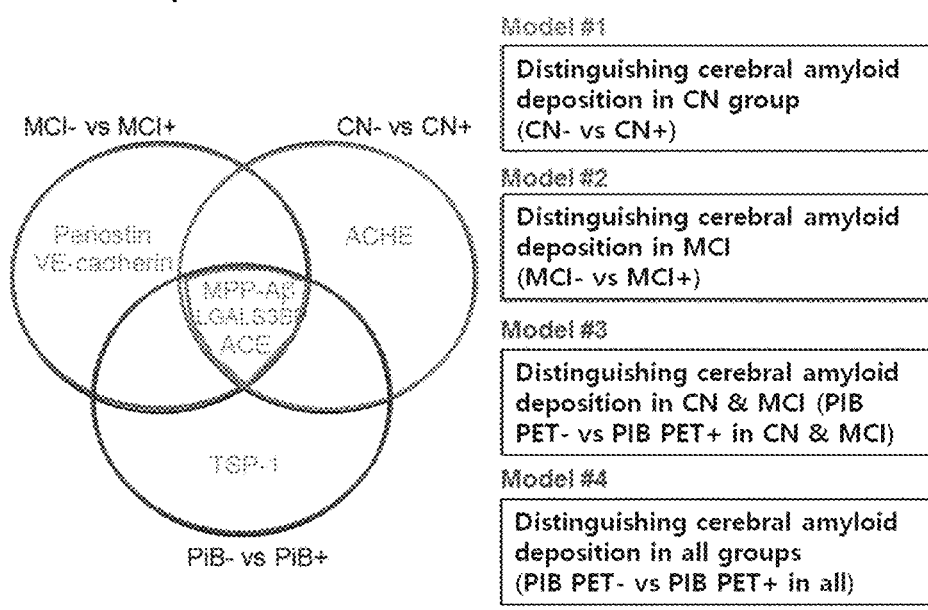
Figure 1C:
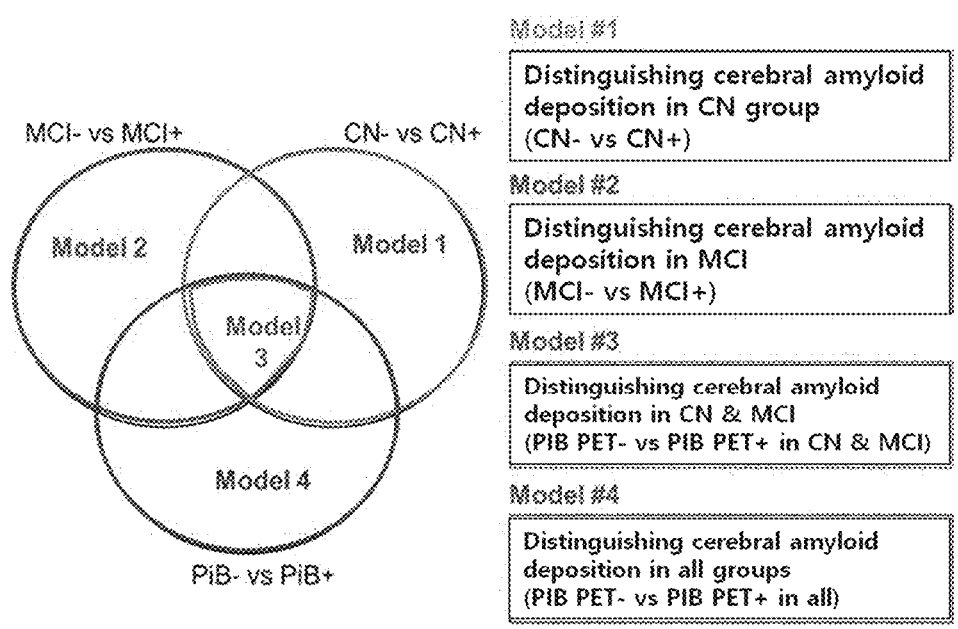
Figure 2A:
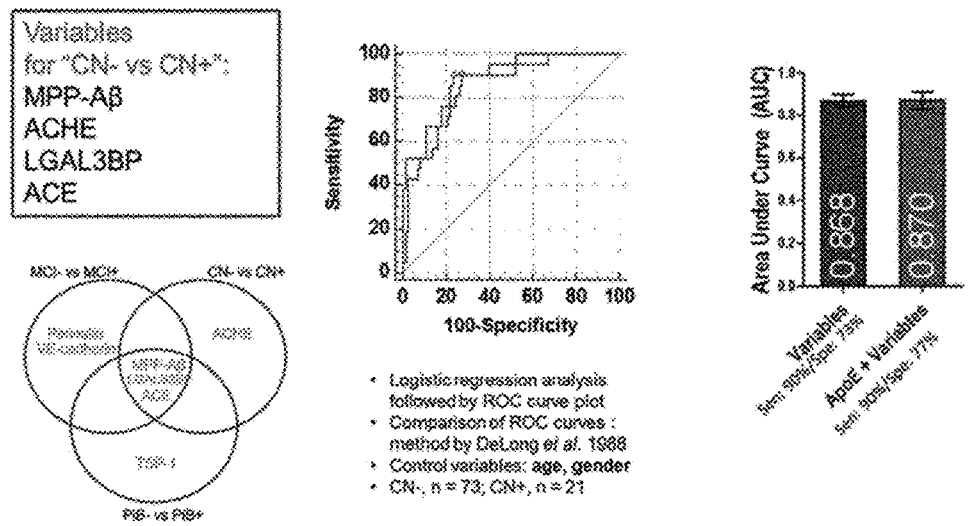
FIG. 2a shows the results of distinguishing features of brain amyloid beta accumulation (Aβ+vs Aβ−) in the normal cognitive function group (CN) as a model 1.
Figure 2B:
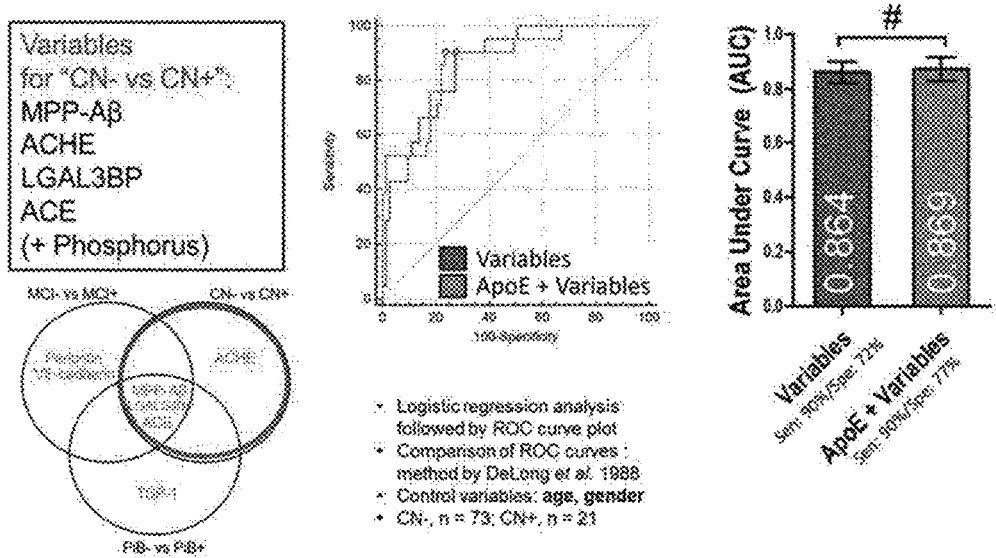
FIG. 2b is the same as FIG. 2a, but with phosphorus as an additional biomarker.
Figure 3A:
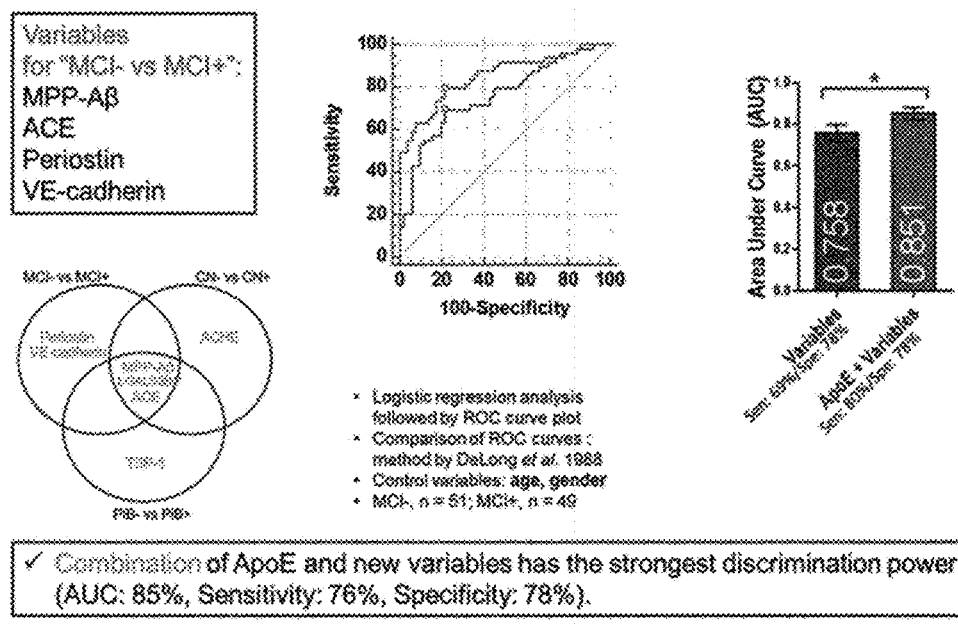
FIG. 3a shows the results of distinguishing features of brain beta amyloid accumulation (Aβ+vs Aβ−) in patients with mild cognitive impairment group (MCI) as a model 2.
Figure 3B:
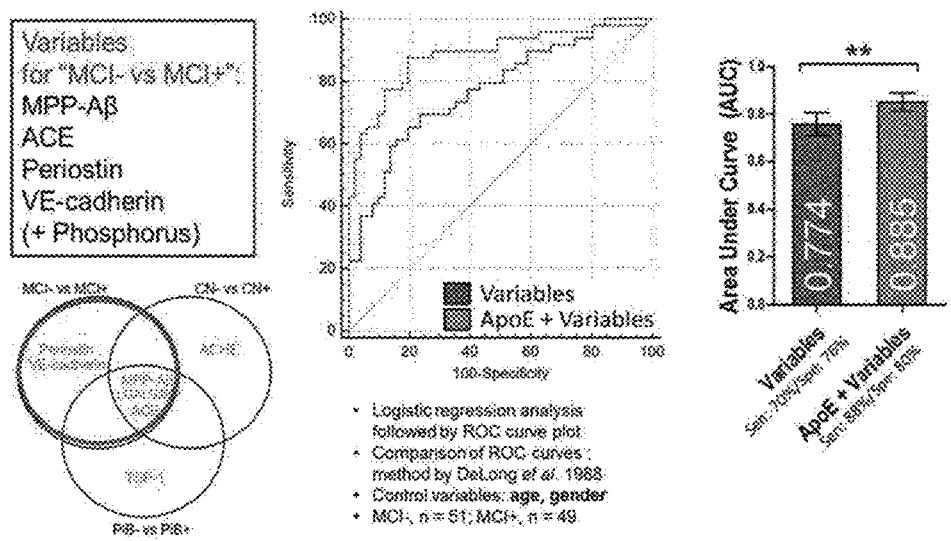
FIG. 3b is the same as FIG. 3a but with phosphorus as an additional biomarker.
Figure 4A:
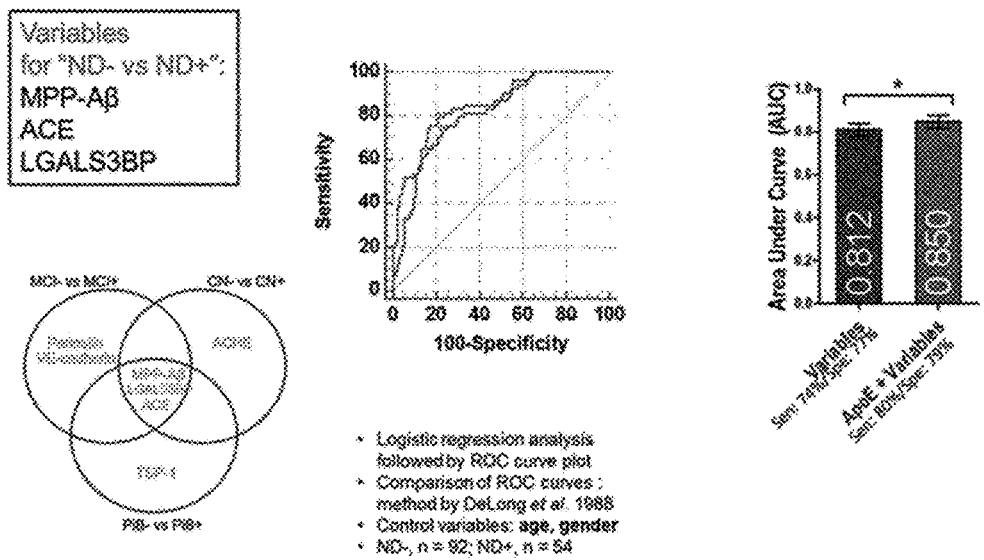
FIG. 4a shows the results of distinguishing features of brain beta amyloid accumulation (Aβ+vs Aβ−) in the non-dementia group (CN and MCI) as a model 3.
Figure 4B:
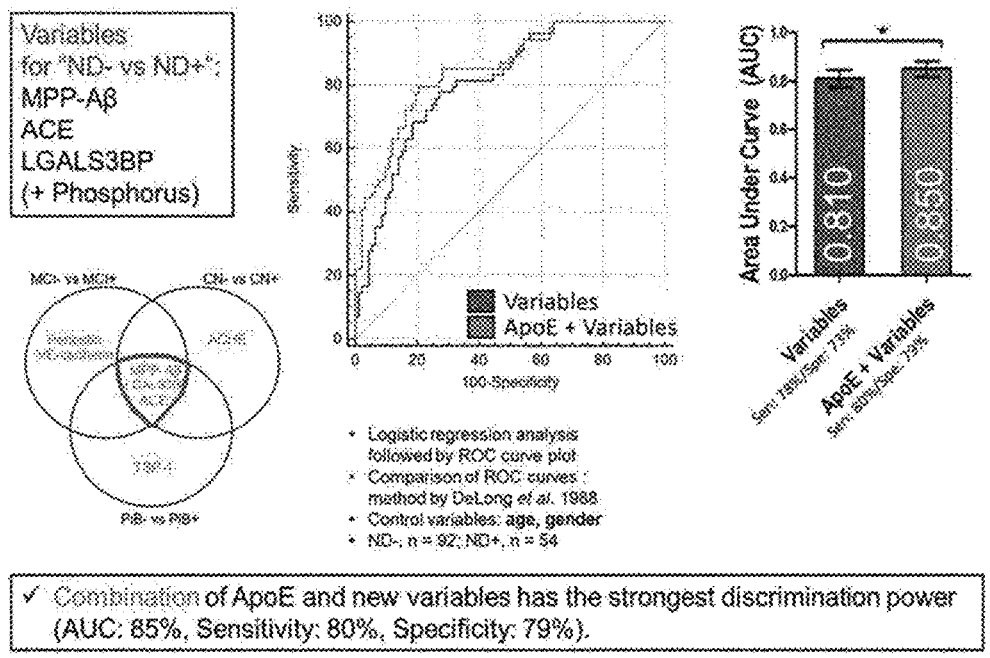
FIG. 4b is the same as FIG. 4a but with phosphorus as an additional biomarker.
Figure 5A:
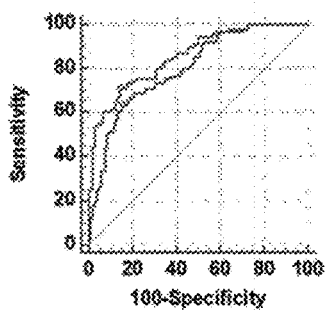
FIG. 5a shows the results of distinguishing features of amyloid beta accumulation in brain (Aβ+vs Aβ−) in all subjects regardless of cognitive function as model 4.
Figure 5A:
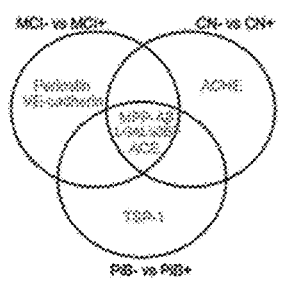
Figure 5A:
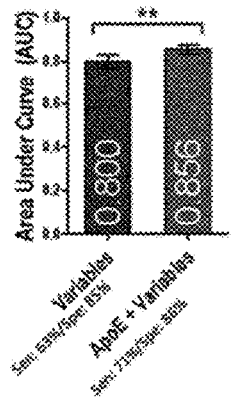
Figure 5B:
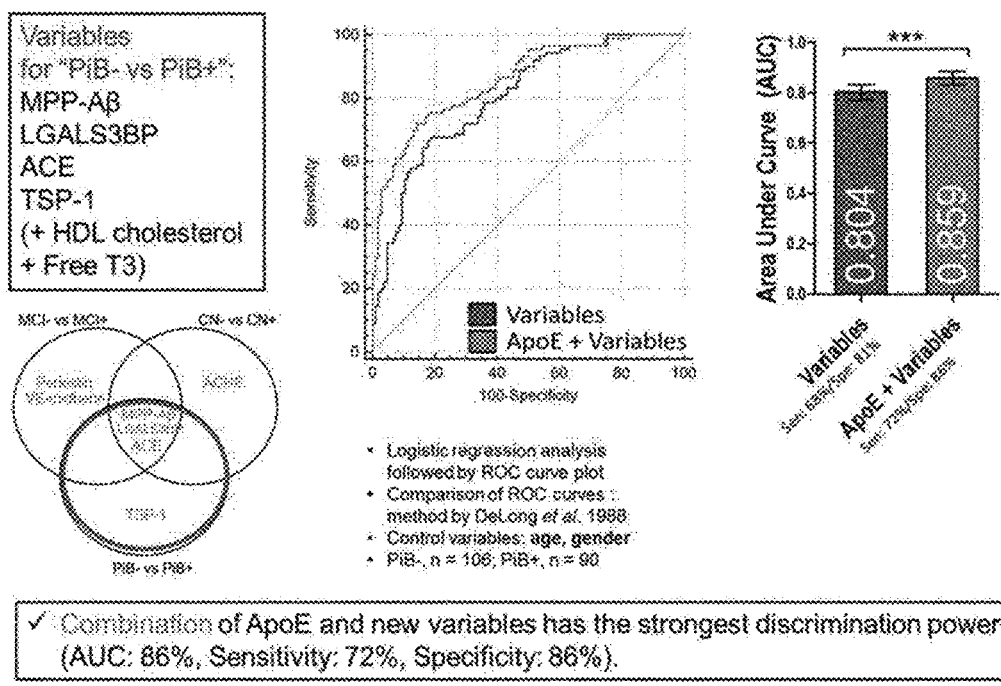
FIG. 5b is the same as FIG. 5a, but with HDL cholesterol and free triiodothyronine (T3) as additional biomarkers.
Figure 6:
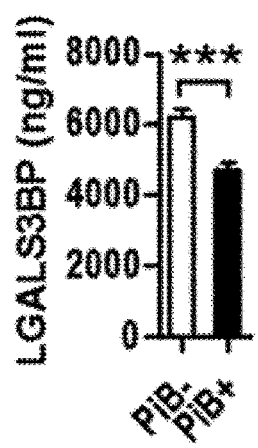
FIG. 6 shows the results of quantifying LGALS3BP in blood by ELISA in normal cognitive function (CN), mild cognitive impairment (MCI), Alzheimer's disease dementia (ADD), and all group (PIB− vs PIB+).
Figure 6:
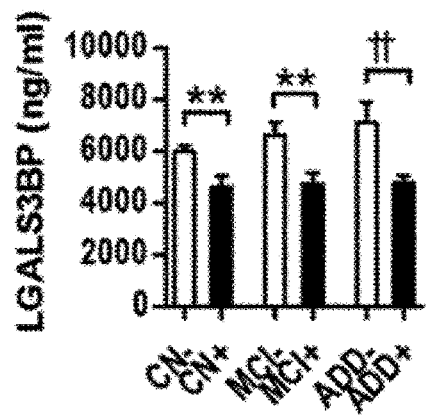

According to the present application, the concentration of the blood marker according to the present invention is highly correlated with the accumulation of amyloid beta plaque, which is known as a causative agent of Alzheimer's dementia, based on brain imaging results of PIB-PET widely used for the diagnosis of Alzheimer's dementia. That is, in the PIB-PET positive subjects, the concentration of the markers according to the present application was significantly increased or decreased in the blood, compared with the results of the PIB-PET negative subjects. That is, referring to FIG. 1a, Periostin is statistically significantly increased in the PIB-PET positive subjects, while LGALS3BP, ACE, AChE, TSP1, VE-cadherin are all statistically significantly decreased in the same subjects. This indicates that the markers according to the present application can be effectively used for beta amyloid accumulation in the brain. In addition to the markers herein, the additional markers used are phosphorus, free T3 and HDL cholesterol. As compared to the results of normal control or PIB-PET negative subjects, the blood phosphorus, Free T3 concentration is lowered in PIB-PET positive subjects, the concentration of HDL cholesterol is significantly higher in PIB-PET positive subjects.

As used herein, the term "detection reagent" is a reagent capable of detecting or quantifying a marker according to the present application, for example, a substance capable of detecting the marker of the present disclosure at a nucleic acid level such as a gene or mRNA, and at a protein level, or else other detection reagent may be made to what is described in the Examples herein.

As used herein, "detection" includes quantitative and/or qualitative analysis, including the detection of presence, absence, and expression level detection. Such methods are known in the art and are described herein, including the following examples. Those skilled in the art will, in consideration, be able to select the appropriate method for the practice herein. For example, the method of detecting each marker according to the present application may refer to the method described in the examples herein.

For example, methods and reagents for detecting protein levels are known and include antigen-antibody reactions, substrates that specifically bind to the markers and receptors or ligands or cofactors that specifically interact with the markers. Reagents or materials that specifically interact with or bind to the markers of the present disclosure may be used with chip technology or nanoparticle technology. In one embodiment, the antigen-antibody reaction can be performed one of following methods, enzyme-linked immunosorbent assay (ELISA), radioimmunoassay (RIA), sandwich ELISA, Western blot on polyacrylamide gel, Immuno dot blotting assay, Immuno-fluorescence assay (IFA), Immunochemiluminescence Assay, Immunohistochemical staining, Rapid Immunochromatography, antigen-antibodies using beads or discs reaction (X-MAP technology) etc.

According to an embodiment of the present disclosure, the composition according to the present disclosure comprises a reagent required for the detection of the marker at the protein level. For example, reagents detectable at the protein level may include monoclonal antibodies, polyclonal antibodies, substrates, aptamers, receptors, ligands, cofactors, and the like. Such reagents can be incorporated into nanoparticles or chips as needed.

According to another embodiment of the present invention, the detection reagent comprises an antibody, and the detection of the marker of the present application is performed using an antibody molecule that specifically binds thereto.

Antibodies that can be used herein are polyclonal or monoclonal antibodies, preferably monoclonal antibodies. Antibodies may be made by commonly used methods in the art, such as fusion methods [Kohler and Milstein, (1976) European Journal of Immunology, 6: 511-519], recombinant DNA technology (U.S. Pat. No. 4,816,56) or phage antibody library methods [Clackson et al, (1991) Nature, 352: 624-628 and Marks et al, (1991) J. Mol. Biol., 222: 58, 1-597]. General procedures for antibody production and usage are described in several references followings, [Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; And Coligan, CURRENT PROTOCOLS IN IMMUNOLOGY, Wiley/Greene, N Y, 1991], which are incorporated herein by references.

In another embodiment, the present invention provides a blood sample derived from a test subject that requires the detection of brain amyloid beta accumulation; Quantifying one or more markers selected from the group consisting of Periostin, VE-cadherin, Acetylcholinesterase (ACHE), Thrombospondin-1 (TSP-1), plasma amyloid beta, LGALS3BP (Lectin, galactoside-binding, soluble3 binding protein) and ACE (Angiotensin I converting enzyme) in the blood sample; Among the markers, plasma amyloid beta, LGALS3BP, ACE and AChE are for detecting brain amyloid beta accumulation in the normal cognitive function group; Among the markers, plasma amyloid beta, LGALS3BP, ACE, Periostin and VE-cadherin are for detecting brain amyloid beta accumulation in the mild cognitive impairment group; Among the markers, plasma amyloid beta, LGALS3BP, and ACE are for detecting brain amyloid beta accumulation in the non-dementia group including the cognitive normal group and the mild cognitive impairment group; Among the markers, plasma amyloid beta, LGALS3BP, ACE and TSP-1 are for detecting brain amyloid beta accumulation in blood from all progress stage groups, including non-dementia and dementia groups; And a method for detecting a marker from a subject's specimen includes steps for correlating the detected amount of marker with amyloid beta accumulation or other related disease diagnosis or prognosis in the brain of the subject.

In one embodiment, the amyloid beta is used that has been treated with MPP as mentioned above.

In another embodiment, the method according to the present disclosure may further comprise the use of an ApoE genotype as an additional marker.

There are three types of ApoE genes, ApoE2, ApoE3 and ApoE4, which are already widely known risk factors for people with ApoE4 who are likely to develop AD than other ApoE carriers. Therefore, it is known to be a genetic risk factor of AD, and this genetic test can predict the incidence of AD. ApoE (Apolipoprotein E) has three alleles called E2 (cys112, cys158), E3 (cys112, arg158), and E4 (arg112, arg158). The genotype of an individual exists in 6 different types such as E2/E2, E2/E3, E2/E4, E3/E3, E3/E4, or E4/E4 types. Among these alleles, E4 alleles are found in about 20% of the population and are known to increase the risk of developing Alzheimer's dementia. According to the present application, the specificity and sensitivity may be improved when the ApoE genotype marker is used in addition to the markers according to the present application. Detection of ApoE genotype can be performed using known methods, and those skilled in the art will be able to select the appropriate one. In one embodiment, according to the present invention, a PCR method using allele specific primers may be used as disclosed in the Examples.

In another embodiment, the method according to the present disclosure may further comprise the use of one or more of the usual blood test items, phosphorus, free T3, HDL cholesterol as additional biomarkers. For example, the method using one or more additional biomarker consists of HDL cholesterol, free T3, and phosphorus may be referred to, for example, the methods described in the Examples herein.

The method according to the present invention is particularly used for the diagnosis of brain amyloid beta accumulation associated with brain amyloid beta accumulation, the brain amyloid beta accumulation disease is Alzheimer's disease, Parkinson's dementia, Lewy body dementia, Huntington's dementia, or preclinical Alzheimer's disease, Down syndrome, or cognitive impairment.

The method according to the present invention also includes the diagnosis of severity of cognitive impairment of brain amyloid beta accumulation disease.

In addition to the biomarker analysis result, the present method may further use non-protein clinical information of the patient, that is, clinical information other than the marker. Such non-protein clinical information may include more than one of followings, but not limited to list here, the age, sex, weight, diet, body mass, underlying disease, magnetic resonance imaging (MRI), single-photon emission computed tomography (SPECT), mini-mental status examination (MMSE) or positron emission tomography (PET) of a subject.

The method includes correlating the detection result of the marker with the diagnosis or prognosis of a disease associated with amyloid beta plaque accumulation in the brain, and according to one embodiment, the associating step means data processing from comparison of the amount of each marker of test subject with the amount of control.

In one embodiment, the results of test subject group herein are compared with the results of the control group (the value determined in the blood sample of PIB-PET negative). For example, comparing the increase and decrease of the results between test subject and control group, base on this, the brain amyloid beta accumulation is predicted or diagnosed.

For example, when one or more of the markers according to the present application are significantly increased or decreased in comparison to the value of the control group, information may be provided for diagnosing the accumulation of plaque or the occurrence of the disease in the subject.

For example, the associating step compares the biomarker level of the subject group with the quantitative result including the value determined in the blood sample of test subject or normal control group (PIB-PET negative). In comparison, Periostin is increased; LGAL, ACE, AChE, TSP1, and VE-cadherin are all decreased compared to the control group in the beta amyloid accumulated in the brain. Also, for example, the associating step compares the amount of each marker determined in the subject group with the quantitative result determined in the blood sample of test subject or normal control (PIB-PET negative). Compared with the control group, phosphorus and free T3 levels are lowered and HDL cholesterol level is significantly higher in subjects with beta amyloid accumulated in the brain.

For example, brain amyloid beta accumulation can be predicted when one or more markers are used simultaneously (multi-marker) and the degree of change such as increase or decrease is calculated as a single value. Combination of the multiple markers of models 1 to 4 according to the present application for amyloid beta accumulation in patients according to the degree of cognitive function (normal cognitive function, mild cognitive impairment group, Alzheimer's dementia group) is described, for example, in Example 2 herein. Using the formula as disclosed in the above, the cutoff value can be determined and used to determine brain amyloid beta accumulation.

In addition, according to the exemplary embodiment of the present invention, the step of associating a sample of a normal control group with a subject, and after setting a threshold value for predicting plaque accumulation or diagnosing a disease for each marker, the detection result of the subject can be compared with the threshold value. For example, as described in the Examples herein, the threshold of each marker that determines whether brain amyloid beta plaques accumulate, i.e., negative and positive, i.e., PIB-PET negative and positive, is determined by the MedCalc program. It can be determined based on the Youden's index determined by the ROC curve analysis using. The threshold value indicates positive amyloid beta plaque accumulation in the brain, and may be used for screening PIB-PET test subjects and diagnosing diseases related to brain amyloid beta plaque accumulation.

The PIB-PET test is not only inconvenient for the patient but also expensive and time-consuming, so the screening process for people with high possibility of accumulating amyloid plaque is urgently needed.

In another embodiment the method according to the present invention is intended to provide information on whether a test subject in need of judging amyloid beta plaque accumulation in the brain, including Alzheimer's dementia, needs information on whether a PIB-PET test of the brain is required. Providing a blood sample from subjects; quantifying the marker according to the present application in the blood sample; and determining the subject as a PIB-PET test subject by comparing the concentration of the marker of subject with that of a control judged to be negative for the PIB-PET test as a control; providing methods for detecting markers for screening subjects in need of PIB-PET testing. For example, in the blood test using the marker according to the present application, it is not necessary to test the PIB-PET image when it is determined that amyloid beta is not accumulated in the brain. If it is determined that beta amyloid has accumulated in the brain, PIB-PET imaging can be done to confirm the diagnosis.

In addition, with respect to each of the markers in the above-described method according to the present application may refer to the above.

Hereinafter, examples are provided to help understand the present invention. However, the following examples are provided only to more easily understand the present invention, and the present invention is not limited to the following examples.

Example 1. Biomarkers Excavation and Measurement Methods 1-1. Cohort of Subject's Recruitment and Screening Assessment Subjects were recruited through an outpatient/dementia support center/poster, and clinical/neuropsychological evaluation was conducted to evaluate screen whether the possible candidates met the criteria of selection or exemption. At this time, the subjects that satisfied the criteria for selection and did not meet any criteria for exemption were chosen to conduct the Baseline Evaluation (detailed evaluation), the subjects that did not fall into this category were considered to have failed the screening.

The criteria for selection were based on clinical diagnostics (see Alzheimer's Dementia Diagnostic Clinical Criteria by National Institute on Aging and the Alzheimer's Association (NIA/AA), Nihon Rinsho. 2016 March; 74 (3): 386-94, etc.) meaning Mild Cognitive Impairment clinical criteria and Alzheimer's dementia clinical criteria were applied. With Mild Cognitive Impairment, the z-score of certain characteristics had to be lower than the cut-off to meet the selection criteria. The z-score is a statistic value found by considering the subject's age, sex, and years of education with the original score, through this calculation: (original score−average)/(standard deviation).

The baseline evaluation was conducted on the group that passed the screening test, by conducting brain imaging evaluation (PET-MRI), blood tests, detailed clinical evaluation and detailed neuropsychological examinations, and additional surveys.

A total of 429 patients with normal, mild cognitive impairment, and Alzheimer's dementia were selected through the above steps. After fasting for 12 hours, blood was collected at the hospital in the morning and PIB-PET scan was performed as follows. The collected blood samples were used to detect and quantify proteins.

1-2. PIB-PET Image Scan Participants measured T1-weighted MR and three-dimensional PIB-PET images using a Biograph mMR scanner (Siemens, Washington, D.C., USA). After 40 minutes since an intravenous injection of 555 MBq of 11C-PiB, a 30 minute transmission scan was retrieved. The data went through an iteration method (21 subsets repeated 6 times) to create a 256×256 image matrix, which was corrected factoring in consistency, very high frequency echo time 9UTE)—basic damping (attenuation), and decay reduction. Sagittal T1-weighted (repeat time=1370 ms; echo time=1.89 ms; observational field of vision, 250 nm; 256×2561.0 mm thickness matrix) was obtained. The imaging data was processed by using the Statistical Parametric Mapping 8 (SPM8) in MATLAB 2014a (MathWorks, Natick, Mass.). PIB-PET data were co-registered with individual T1 images to calculate the modification parameters for the standard Montreal Neurological Institute (MNI) template.

Individual Brain Atlases using Statistical Parametric Mapping Software (IBASPM) were used to calculate inverse transformation parameters that transform coordinates from automatic anatomic labeling (AAL) 116 atlas (Weiss, 1989) into individual spaces for each individual (resampling voxel size=1×0.98×0.98 mm). Using the individual AAL116 atlas obtained from the T1-coregistered PIB-PET image, the average 11C-PIB uptake of the local brain was calculated, and for normalization the statistical data on the 11C-PIB uptake in the gray matter of the cerebellum was used. In order to define the ROI (region of interest), the AAL algorithm and region-combining method (Yaffe et al., 2011) was applied, and the regions of the brain were separated into the frontal area, lateral parietal lobe, posterior cingulate-precuneus (PC-PRC), and the lateral temporal region where 11C-PIB significant retention was reportedly found in (Klunk W. E. et al., 2004. Imaging brain amyloid in Alzheimer's disease with Pittsburgh Compound-B. Ann Neurol 55(3), 306-319.). The SUVR (standardized uptake value ratio) value was calculated by dividing the average value of every voxel within the ROI with the average cerebellum uptake value. If the SUVR value was over 1.4 in at least one of the 4 ROIs (i.e., frontal, lateral temporal, lateral parietal, and PC-PRC) the individual was classified as PIB positive (PIB+), and if the SUVR values in all 4 ROIs were below 1.4, the individual was classified as PIB negative (PIB−). While PIB-represents an individual with negative amyloid deposition, PIB+ represents an individual with positive amyloid deposition. The SUVR for the entire brain was calculated by dividing the average value of every voxel within the ROIs with the average cerebellum uptake values in the same imaging data.

The results of the PIB PET scan showed that 282 out of 429 were PET negative, with 147 PET positive. These PIB PET results (positive/negative distinction, quantitative values of PIB-PET which is SUVR) and the analysis of the ROC curve made through a quantitative analysis of markers in the blood were used to examine correlation, specificity, sensitivity, and AUC (see Example 2, FIG. 1 to FIG. 5).

1-3. Selection of Blood Biomarker

Using samples from 10 individuals from each group, a global and glycosylation proteomics analysis (Li et al, 2014, Journal of Proteome Res 13, 3488-3497) was conducted through mass spectrometry to identify 3,948 protein groups. These results were run through a Bioinformatics analysis (Kang et al., 2016, Journal of Alzheimer's disease 53, 1563-1576) to select possible biomarker proteins that differed between the groups. The order of likelihood of a protein being a possible biomarker was determined by the amount it increased or decreased in individuals that were brain amyloid beta positive with mild cognitive impairment or Alzheimer's disease, compared with the normal group which was brain amyloid beta negative. The amount of increase/decrease was measured by quantitative analysis of the blood samples through the ELISA method, on which the selection of the marker was based on. As a result of quantification, the marker of the present application was selected.

1-4. Measurement of Blood Protein Concentration (ELISA, Enzyme-Linked Immunosorbent Assay)

The concentration of amyloid beta in blood was measured using the X-MAP technique after treatment of the plasma pretreatment composition. The plasma pretreatment composition comprises the protease inhibitor and the phosphatase inhibitor at 1:1 (v/v). In addition, MPP may be a mixture of Protease inhibitor cocktail (PIC): Serine protease inhibitor (PMSF): Phosphatase inhibitor cocktail I: Phosphatase inhibitor cocktail II at the ratio of 1:1:1:1 (v/v). The protocol of protein pretreatment is described in detail in a licensed patent [METHOD FOR MONITORING CLINICAL AND PATHOLOGICAL ALZHEIMER'S DISEASE USING AMYLOID BETA CONCENTRATION IN PLASMA, Korea patent no. 10-1786859].

Briefly describing the measurement method, the INNO-BIA plasma Aβ forms kit (Fujirebio) was used to simultaneously measure the concentrations of A1342 and A1340. Beads bound to the antibody were first passed through the plate, the beads were mounted on the plate, and then plasma sample treated with MPP was incubated for 30 minutes in the plate along with the standard samples. After 30 minutes incubation, adding the beads with conjugated antibody, plate was further incubated for one day. The next day, after washing the plate, the detection antibody was added and incubated for 1 hour. Finally, the reading solution was added to measure the amyloid beta pretreated with MPP in plasma using X-MAP technology.

The concentrations of the plasma proteins LGALS3BP, ACE, AChE, TSP1, Periostin, and VE cadherin were measured by ELISA (enzyme-linked immunosorbent assay). This is an experimental method of measuring the amount of a particular protein in a biological sample using antigen-antibody reactions and colorimetric analysis. Detailed test methods are described in the instructions for each product. (LGALS3BP, Abnova Company, KA0140; ACE, R&D Company, DACE00; AChE, R&D Company, DACHE0; TSP1, R&D Company, DTSP10; Periostin, CUSABIO Company, CSB-E16444h; VE-cadherin, R&D Company, DCADV0). Briefly, plasma samples and standard samples were placed in a plate coated with a target antibody and incubated for one and a half to two hours at room temperature. After incubation, each well was washed five times with a wash solution, the conjugated antibody was added thereto, and then again incubated for 2 hours. After washing each well once again, Tetramethylbenzidine (TMB) solution was added to measure HRP activity. After 30 minutes, stop solution was added to prevent saturation, and signal was measured at 450 nm from plate.

1-5. Blood Test (1) Cholesterol: Colorimetric Method

The test equipment used was ADVIA 1800 Auto Analyzer (Siemens, USA) and the test reagent was HDL-Cholesterol (Siemens, UK). Wherein, the reference value is 40-60 mg/dL.

The principle of the test method is as follows. The HDL cholesterol direct measurement (D-HDL method) measured HDL cholesterol in serum and plasma without prior separation, based on procedures developed by Izawa, Okada, and Matsui. Cholesterol from non-HDL particles was liberated and removed at the first step of the reaction. HDL particle-derived cholesterol was released in the second step by detergent of R2, and HDL cholesterol was measured by Trinder reaction.

The method consists of two steps followings:

a. Removal of Chylomicron, VLDL-Cholesterol, and LDL-Cholesterol by Cholesterol Esterase and Cholesterol Oxidase. The peroxide produced by the oxidase was removed with catalase.

b. Specific measurement of HDL-cholesterol after HDL-cholesterol release by surfactant with Reagent 2. The catalase of former step was inhibited with a sodium azide of R2. The intensity of quinoneimine produced in the Trinder reaction, measured at 596 nm, is directly proportional to cholesterol concentration.

(2) Free T3: Chemiluminescence Immunoassay, CIA

The test equipment used was ADVIA Centaur XP (Siemens, USA) and the test reagent was Free T3 (Siemens, USA). Wherein, the reference values were 3.3-5.2 pg/mL for 1-23 months old, 3.3-4.8 pg/mL for 2-12 years old, 3.0-4.7 pg/mL for 13-21 years old, and 2.3-4.2 pg/mL for over 21 years old. The principle of the test method is as follows. Two-step sandwich immunoassay was performed using chemiluminescent. FrT3 and FrT3 reagents in serum were competitively combined to form paramagnetic particles in the solid phase and relative light units (RLUs) generated by binding acridinium ester-labeled mouse anti-T3 antibody of Lite reagent was measured.

(3) Phosphorus: Colorimetric Method

The test equipment used was ADVIA 1800 Auto Analyzer (Siemens, USA) and the test reagent Pi (Siemens, UK). The reference value is 2.4-5.1 mg/dL. The principle of the test method is as follows. Inorganic phosphorus reacts with ammonium molybdate in the presence of sulfuric acid to produce a non-reducing phosphomolybdate complex, which was measured at 340/658 nm as a terminating reaction.

1-6. MPP-Treated Amyloid Beta Measurement Assay

Reference was made to the method described in Korean Patent Publication No. 2016-0129444 [METHOD FOR MONITORING CLINICAL AND PATHOLOGICAL ALZHEIMER'S DISEASE USING AMYLOID BETA CONCENTRATION IN PLASMA]. The reagents used are as follows. MPP mixture consist of equal proportion of following reagents was used, protease inhibitor cocktail (PI), phenylmethanesulfonylfluoride (PMSF, a serine protease inhibitor; Sigma Aldrich, CA, USA) and phosphatase inhibitor cocktail I and II (PPI I and II; AG Scientific, Inc., CA, USA). Aβ peptides are provided by American Peptide Company, Inc. (Sunnyvale, Calif., USA) and human serum albumin was purchased from Sigma Aldrich.

Blood Sample

After fasting overnight, venous blood was collected and collected on K2 EDTA tubes (BD Vacutainer Systems, Plymouth, UK) and centrifuged at 700×g for 5 minutes at room temperature to separate plasma and obtain in 15 ml centrifuge tubes. To obtain a high purity sample, the plasma sample was centrifuged again under the same conditions, aliquoted and immediately frozen to −80 degrees.

Aβ Measurement

In order to simultaneously measure blood levels of A1342 and A1340, the INNO-BIA plasma Aβ forms kit (Innogenetics, Gent, Belgium) was used according to the manufacturer's method. In summary, plasma was diluted three-fold with MPP treated plasma dilution buffer or MPP untreated plasma dilution buffer and left at room temperature for 30 minutes. The filter plates were then washed and the diluted bead mix was transferred to each well of the plate. Plates were then carefully dried and washed and 25 μL of Conjugate 1 Working Solution A and 75 μL of standard, blank, control and plasma samples were added to each well. The plates were then incubated overnight at 4 degrees Celsius and 100 μL detection solutions were added to each well. After 1 hour the plates were washed and reading solution was added to each well. Plasma amyloid beta concentrations were measured using X-MAP technology (Bioplex 200 systems; Bio-rad, Hercules, Calif., USA).

1-7. ApoE Genotype Analysis: ASP-PCR: Allele Specific Primer-Polymerase Chain Reaction Using a primer capable of specifically amplifying alleles with specific gene mutations, a method for identifying specific gene mutations with or without an amplification reaction was used. Specifically, DNA was extracted from the sample using the Salting out method. PCR reaction with ApoE PCR Master Mixture (Biocore) was performed and then analyzed PCR reaction product using the manufacturer's method. The size of PCR products by type is listed in Table 2. ApoE4 carrier has a high risk for Alzheimer's dementia. In other words, E4/4 carrier is the most at risk of AD, followed by E4/3.

TABLE 2

| TYPE | E2/2 | E2/3 | E2/4 | E3/3 | E3/4 | E4/4 |
|---|---|---|---|---|---|---|
| 710 bp | + | + | + | + | + | + |
| 597 bp | − | − | + | − | + | + |
| 461 bp | − | + | + | + | + | + |
| 315 bp | + | + | + | − | − | − |
| 179 bp | + | + | + | + | + | − |

Example 2. Beta Amyloid Accumulation Discrimination According to the Degree of Cognitive Function Using the Biomarker of the Present Application in Combination Biomarkers, Periostin, VE-cadherin, Acetylcholinesterase (ACHE), Thrombospondin-1 (TSP-1), Lectin, galactoside-binding, soluble3 binding protein (LGALS3BP), and Angiotensin I converting enzyme (ACE), are quantified in the blood of each patient of Example 1 by ELISA assay as described above. And serum amyloid beta was quantified in blood by X-MAP technology (2017 Park et al., Alzheimer's research & Therapy).

In FIGS. 2 to 5, after combining the markers that are particularly effective in the blood of the patients of each group of cognitive normal functional group, mild cognitive impairment group and Alzheimer's dementia group, a value expressed as pi or an integrated index was calculated through logistic regression as shown in the following equation. According to the above values, the analysis was performed to predict whether the brain amyloid beta accumulated. Determination of positive or negative of brain amyloid beta accumulation, when the calculated indices Pi value increased above the cut off value or not, respectively. The integrated index Pi values were calculated using Youden's J statistic (Ruopp et al. Biom J. 2008 June; 50 (3): 419-430). In addition, specificity and sensitivity were determined through ROC curve analysis using the integrated index to calculate the prediction effectiveness/accuracy.

In addition, the combination of the markers of FIGS. 2 to 5 was determined using a combination with the genotype test of ApoE.

The combination of each of the markers of FIGS. 2 to 5 above was also determined in combination with phosphorus, free T3 and/or HDL cholesterol, in the presence or absence of ApoE.

$$\ln\{pi/(1-pi)\}=\beta_0+\beta_1 x_{1,i}+\beta_2 x_{2,i}+\ldots+\beta_m x_{m,i} \quad \text{[Equation 1a]}$$

($pi$: predictive probability, $\beta_0$: constant, $\beta_{1-m}$: coefficient of variable)

The number of variables varies depending on the number of markers used, and the equation for six markers is the same as follows, $$\ln\{pi/(1-pi)\}=\beta_0+\beta_1 x_{1,i}+\beta_2 x_{2,i}+\beta_3 x_{3,i}+\beta_4 x_{4,i}+\beta_5 x_{5,i}+\beta_3 x_{6,i} \quad \text{[Equation 1b]}$$

($\beta_0$: regression equation of the model constant, $\beta_1$: the ratio coefficient of MPP-Aβ42/40, $\beta_2$: coefficients of LGAL, $\beta_3$: coefficients of ACE, $\beta_4$: coefficients of TSP-1, $\beta_5$: coefficients of AChE, $\beta_6$: coefficients of Periostin, $x_1$: ratio values of MPP-Aβ42/40, $x_2$: the quantitative value of LGAL, $x_3$: the quantitative value of ACE, $x_4$: the quantitative value of TSP-1, $x_5$: the quantitative value of AChE, $x_6$: the quantitative value of Periostin)

Pi value in equation 1a was calculated from the following equation.

$$\text{logit}(Pi) = \ln\left(\frac{Pi}{1-Pi}\right), \quad Pi = \frac{1}{1+e^{-\text{logit}(pi)}} \quad \text{[Equation 2]}$$

Plasma amyloid beta concentration obtained by X-MAP technology (2017 Park et al., Alzheimer's research & Therapy), blood protein concentration of each biomarker obtained on the basis of ELISA experiments were determined using multiple biomarker variables, were utilized in statistical analysis.

Statistical analysis was performed using Graphpad Prism 5 (GraphPad Software, Sandiego, Calif., USA) and MedCalc (MedCalc Software, Ostend, Belgium) software. All data are expressed as mean±standard error of the mean (SEM). In addition, an unpaired student's t test was used to compare the PIB-PET positive or negative group by protein concentration in plasma. After ANOVA analysis, Tukey's multiple comparison assay was performed with GraphPad Prism 5. In order to evaluate the performance of the diagnostic test, logistic regression according to the ROC (Reveiver Operating Characteristic) curve analysis was performed with MedCalc. In addition, ROC curve and AUC (Area under the curve) were measured using Wilcoxon statistics. In the multiple logistic regression analysis, each variable was used as an independent variable to derive the final model, and covariates such as gender and age were used as correction variables.

In addition, a new multiple variable derived from logistic regression analysis was used to screen brain amyloid accumulation through ROC curve analysis, and the cut-off value (Criterion value) obtained from the regression analysis was used as a reference point for distinguishing PIB-PET positive and PIB-PET negative.

The results are shown in FIGS. 2 to 5. FIGS. 2 to 5 show AUC (Area Under curve) values that determine specificity, sensitivity, and accuracy of each model. In addition, the specificity and sensitivity of the case of additionally containing ApoE are improved.

The Pi cutoff values determined by Youden's J statistic in each model are as follows:

Model 1: 0.63, Model 1 (with ApoE): 0.67; Model 2: 0.46, Model 2 (with ApoE): 0.68; Model 3: 0.51, Model 3 (with ApoE): 0.59; Model 4: 0.49, Model 4 (with ApoE): 0.58.

However, the cutoff value may vary depending on, for example, an test purpose. For example, if performed for screening purposes in a health examination, cutoff values may be set low to cover all possible subjects.

All technical terms used in the present invention, unless defined otherwise, are used in the meaning as commonly understood by those skilled in the art in the related field of the present invention. The contents of all publications described herein by reference are incorporated into the present invention.

What is claimed is:

1. A method for detecting brain amyloid beta accumulation in a subject with normal cognitive function and who has not been treated with an Acetylcholinesterase (AchE) inhibitor, comprising: obtaining a blood sample from the subject and quantifying the level of biomarkers comprising AchE, plasma amyloid beta, Lectin galactoside-binding soluble3 binding protein (LGALS3BP) and ACE (Angiotensin I converting enzyme) in the sample; and performing a positron emission tomography (PET) test using Pittsburgh compound B (PIB) on the subject who has decreased levels of LGALS3BP, ACE, and AChE compared to subjects with normal cognitive function and no brain amyloid accumulation as measured by PIB-PET.

2. The method of claim 1, further comprising determining the Apolipoprotein E (ApoE) genotype of the subject.

3. The method of claim 1, further comprising quantifying the levels of one or more biomarkers selected from the group consisting of phosphorous, High Density Lipoprotein (HDL) and free triiodothyronine (T3).

4. The method of claim 3, wherein the levels of phosphorous and T3 are decreased and the level of HDL is increased in comparison to their levels in the blood from subjects with normal cognitive function and without brain amyloid beta accumulation.

* * * * *